United States Patent [19]
Eriksson

[11] Patent Number: 6,045,708
[45] Date of Patent: Apr. 4, 2000

[54] METHOD FOR CONTROLLING MICROORGANISMS

[76] Inventor: Jan-Olof Eriksson, Midsommarstigen 23, S-931 52 Skellefteå, Sweden

[21] Appl. No.: 09/125,686

[22] PCT Filed: Feb. 13, 1997

[86] PCT No.: PCT/SE97/00224

§ 371 Date: Sep. 2, 1998

§ 102(e) Date: Sep. 2, 1998

[87] PCT Pub. No.: WO97/30589

PCT Pub. Date: Aug. 28, 1997

[30] Foreign Application Priority Data

Feb. 22, 1996 [SE] Sweden ................................. 9600663

[51] Int. Cl.$^7$ ....................................................... C02F 1/72
[52] U.S. Cl. ............................................ 210/759; 210/764
[58] Field of Search ..................................... 210/758, 759, 210/764; 514/613, 715

[56] References Cited

U.S. PATENT DOCUMENTS

| | | | |
|---|---|---|---|
| 4,476,108 | 10/1984 | Kessler et al. | 424/50 |
| 4,753,681 | 6/1988 | Giuffrida et al. | 134/22.17 |
| 4,863,445 | 9/1989 | Mayhan et al. | 604/317 |
| 4,926,795 | 5/1990 | Hamilton et al. | |
| 4,975,109 | 12/1990 | Friedman, Jr. et al. | 71/67 |
| 5,256,182 | 10/1993 | Friedman, Jr. et al. | 210/764 |

FOREIGN PATENT DOCUMENTS

| | | |
|---|---|---|
| 0 047 015 | 3/1982 | European Pat. Off. . |
| 14891 | 6/1902 | Sweden . |
| 20410 | 2/1904 | Sweden . |
| WO 94/24869 | 11/1994 | WIPO . |
| WO 96/03046 | 2/1996 | WIPO . |

OTHER PUBLICATIONS

P.C. Quimby, Jr., et al., "Sodium Carbonate Peroxyhydrate as a new Algicide", STN International File CROPU No. 86–91013, Weed Sci. Soc. Am., 1984.

P.C. Quimby et al., "Sodium–Carbonate Peroxyhydrate as a Potential Algicide", STN International File SCISEARCH No. 88:595776, Journal of Aquatic Plant Management, vol. 26, No. Jul. 1988, pp. 67–68.

"Sodium percarbonate (PCS) will increase detergents' effectiveness in bleaching and stain removal for textiles and tableware, cooking untensils and food containers, and is an algicidal and antibacterial cleaner for hard surfaces such as floors and walls", STN International File PROMT No. 80:45138, Household & Personal Products Industry, Jul. 1980, pp. 77–78.

K. Katayama, "Exfoliation and breakage of slime–using sodium peroxide opt with a strong alkali", File WPI N. 72–69505T.

Koei Chem Co Ltd, "Descoting agent comprising organic and inorganic substances–contains sodium percarbonate as main component and chelating agent and surfactant as minor components", File WPI N. 76–95334X.

S.S. Block, "Disinfection, Sterilization, and Preservation", pp. 654, 677–684, Chemical Disinfection of Medical and Surgical Materials, 2nd Edition, 1977.

*Primary Examiner*—David A. Simmons
*Assistant Examiner*—Betsey J. Morrison
*Attorney, Agent, or Firm*—Young & Thompson

[57] ABSTRACT

A method for the control of microorganisms, especially spore forming organisms, algae, yeast fungi and slime bacteria by bringing an active amount of sodium percarbonate and/or sodium peroxide into contact with the microorganisms.

18 Claims, No Drawings

METHOD FOR CONTROLLING MICROORGANISMS

BACKGROUND OF THE INVENTION

All living microorganisms have developed various protective mechanisms against lethal factors. In group microorganisms this developed resistance is especially significant. Microorganisms can form spores which are more resistent to dryness, heat, chemicals and ultrasonics in comparison with the vegetative maternal cells. The spores can under favourable circumstances grow to become a vegetative cell again.

DESCRIPTION OF THE RELATED ART

Sterilization is a treatment to relieve the object of all living organisms and viruses. A reliable method for a chemical sterilization would also be desirable in several connections. At present there only a few possible substances. The substances must be easily removable from the object after the sterilization and not leave any toxic by-products, and simultaneously have a strong sterilizing effect. Halogen preparations such as chlorine gas, chlorinated lime (for the disinfection of cow houses and chemical toilets) and iodine solutions, organic solvents, heavy metals such as copper sulfate (as a fungicide against fungi and also against algae) and detergents might be mentioned as examples of chemical sterilizing agents.

Spores are a large problem in various fields and there is today no efficient method to kill spores. Certain spores are extremely resistant to dryness, radiation, chemicals and ultrasonics and may survive a cooking (at 100° C.) for several hours. For killing spores an autoclaving procedure is required at 121° C. or a fractionated sterilization; this, however, does not provide complete safety. For a sterilization with dry heat a temperature of 160° C. is required for two hours to kill the spores (Mikrobiologi, Mikrobiologiska institutet, Lund, 1982). These methods of sterilization, however, cannot always be practically performed. Various chemical means are also used to kill spores. Formaldehyde in a water/alcohol-solution is used to a large extent to "sterilize" surgical instruments. Even if the solution is said to have a spore killing effect when used for this purpose, its spore killing effect seems to be somewhat questionable (Kirk Othmer, second edition, volume 2, page 640 <1967>). Saturated dialdehydes and especially glutaraldehyde CHO $(CH_2)_3$CHO have recently been found to have a sterilizing effect, including even a spore killing effect, when used in a water/alcohol-solution in the presence of an alcalizing agent, such as sodium bicarbonate. The bacteria killing effect for vegetative pathogens is said to happen within ten minutes, but an incubation is required during three hours to kill any resistant bacteria spores (Kirk Othmer, second edition, volume 2, page 641 <1967>). Friedl et al have exposed spores from five anaerobic (*Clostridium botulinum, lentoputrescens, perfringens, sporogenes* and *tetuni*) and five aerobic (*Bacillus anthracis, coagulans, globigii, stearothermophilus* and *subtilis*) microorganisms to ethylene oxide which has an intensive microbicidal effect. When exposed at room temperature the dry spores of *Bacillus subtilis* and *Clostridium sporgens* survived during several hours, whereas the other tested organisms were killed after a short period of time. None survived an exposure of eighteen hours (Kirk Othmer, second edition, volume 2, page 641 <1967>). These examples demonstrate the enormous resistance of spores against various chemical control means.

Further examples of difficultly controlled microorganisms are slime bacteria and algae. In the paper pulp industry, for example, these organisms cause severe problems. Microorganisms can be partly controlled by means of chlorine. As the paper pulp industry is forced not to use chlorine any longer and to use hydrogen peroxide instead, the problems with algae and slime bacteria have increased. There exists nowadays no efficient agent against these organisms which is adapted to the environment.

In the brewery industry a great problem is presented by yeast fungi. Yeast fungi are said to present 90 percent of the destruction of carbonated beverages (Kirk Othmer, second edition, volume 2, page 647 <1967>).

Water polluted with bacteria is also causing large problems. Many diseases are spread e.g. via the drinking-water. Potassium permanganate previously used for the disinfection of drinking-water is no longer used due to the toxicity of the manganese residues. (Kirk Othmer, second edition, volume 2, page 623 <1967>). Nowadays various chemicals are used for killing bacteria in drinking-water, especially chlorine, which obviously presents an alternative not acceptable to the environment. An agent which is acceptable to the environment to achieve a water free from bacteria would be very desirable.

From CA-A1-2129489 it is already known to control the growth of microorganisms by means of a combination of non oxidizing biocide and peracetic acid in an acidic solution. Thus, the content of biocide might be reduced. Peracetic acid itself is no providing any especial growth controlling effect and therefore biocides cannot be totally excluded.

It is already known that sodium percarbonate due to its oxidizing and very alkaline properties is corrosive and toxic for living organisms. Due to the presence of hydrogen peroxide, an aqueous solution of sodium percarbonate is very oxidizing. A solution of sodium percarbonate generating a hydrogen peroxide content of 0.1 to 0.25 percent is e.g. sufficient to kill *Salmonella typhosa, E. coli* and *Staphylococcus aureus* within one hour (Kirk Othrner, second edition, volume 2, page 623 <1967>). This content of hydrogen peroxide corresponds to a concentration of sodium percarbonate of about 0.4 to 1.0 percentage by weight. The dry powder of the sodium percarbonate is corrosive and is e.g. used to control parasitic insects in corn stocks. 3.5 percent of this substance between the grains kill insects within fifteen days (Emberi L. C., Nwufo M. I <1990>, Agric Ecosyst Environ 32 <1–2>, 69–76).

SHORT DESCRIPTION OF THE INVENTION

The present inventor has found that sodium peroxy compounds, preferably sodium percarbonate and sodium peroxide, are acting as killers for so-called difficult to control organisms, such as spores, algae, yeast fungi and slime bacteria. This fact is quite new compared with what is already known in the art. Bye the addition of an active amount of sodium percarbonate, bacteria, spores, fungi and algae are killed actively within a short period of time, i.e. from one minute up to one hour, depending on the temperature and the concentration. The sodium percarbonate does not generate any toxic residues and is not affecting the environment.

Furthermore, the present inventor has found, that even very low concentrations of sodium percarbonate are acting as growth preventive agents for bacteria, this discovery providing possibilities for purifying drinking-water with sodium percarbonate.

DETAILED DESCRIPTION OF THE INVENTION

The present inventor has by means of extensive studies discovered that sodium percarbonate, being previously known for its oxidizing and bacteria killing properties, also has an active killing effect for controlling microorganisms as spores, algae, yeast fungi and slime bacteria. The sodium peroxide provides a similar effect as sodium percarbonate, but requires exactly controlled conditions due to the hazards in handling.

The above cited types of microorganisms differ essentially from bacteria as to their resistance to chemical control means. Active agents for killing spores, algae, yeast fungi and slime bacteria are at present not available. Due to the many problems created by these microorganisms in the industry the present invention presents by its unique qualities a very desirable product.

Sodium percarbonate dissolved in water is decomposed into hydrogen peroxide and sodium carbonate. It is the cooperation between the hydrogen peroxide and the sodium percarbonate which is providing the active sterilizing effect. The components for themselves are not providing the same effect. The active solution of sodium percarbonate has a pH value between 8 and 11, especially about 10. One of the advantages of the sodium percarbonate as a means for killing spores, algae, yeast fungi and slime bacteria is that is generates only water and sodium carbonate as residues, i.e. two completely nontoxic products. This means that sodium percarbonate, inspite of its strong sterilizing effect, does not leave any harmful residues possibly affecting the environment in a negative way. In using sodium percarbonate the previously used biocides might be excluded completely, a better result can be achieved and the environment be cared for simultaneously.

Furthermore, the present inventor has found that sodium percarbonate acts as a growth preventing agent for bacteria even at very low concentrations and that the hydrogen peroxide formed by the sodium percarbonate is quickly degraded at elevated temperatures. Thus, the present inventor has discovered that sodium percarbonate provides a very useful product to purify drinking water. The degrading velocity of hydrogen peroxide in a water solution is shown below in example 7. The sodium percarbonate has previously not been used to clean drinking-water. These facts of the effect of sodium percarbonate at low concentrations are new and surprising and open new possibilities for the purification of drinking water. See also examples 2 and 6.

The effect of sodium percarbonate is affected by the temperature and the concentration. An active concentration range for killing:

spores is 5 to 10 percent by weight, preferably 6 to 7 percent by weight, during an incubation of one hour at room temperature, algae, yeast fungi and slime bacteria is 0.3 to 1.0 weight percent, preferably 0.4–0.6 weight percent, at an incubation for 1 hour at room temperature, bacteria is 0.01 to 2.0 percent by weight, concentrations about 0.01 to 0.02 possibly being used at elevated temperatures, and concentrations about 0.8 to 2.0 percent by weight are effective at room temperature. At a concentration of 0.01 to 0.02 percent by weight the sodium percarbonate is at room temperature growth controlling.

Higher concentrations of sodium percarbonate are effective, but provide no further advantages. In all cases lower concentrations may be used at higher temperatures. The expression elevated temperatures relates not to any exact temperature, but to a temperature over 45° C., especially between 45 and 60° C.

The present invention is illustrated more in detail by means of the following example, wherein Example 1 is a test to define the lowest concentration of sodium percarbonate for killing spores at room temperature, Example 2 describes the growth controlling and killing effect of sodium percarbonate at room temperature, Examples 3 to 4 describe examples for possible fields of use for sodium percarbonate as a spore killing agent, Example 5 describes the use of sodium percarbonate as a killing agent for algae, yeast fungi and slime in a cleaning of a tank, Example 6 describes the use of sodium percarbonate as a bacteria killing means for purifying drinking water, Example 7 shows the degrading velocity of hydrogenperoxide in a water solution at various temperatures.

EXAMPLE 1

Killing of spore-forming bacteria (performed by FOA ABC-skydd, Umeå)

Bacteria colonies were isolated from deposits on dairy equipment at Norrmejerier, Umeå. A gram positive, spore-forming bacterium was isolated and was assigned to the genus Bacillus. Further biochemical research identified the species as *B.cereus* alt. *B.mycoides*. *B.mycoides* is as to the majority of its features identical to *B.cereus* and is regarded by many toxin specialists as inseparable from *B.cereus*.

Performance

*B.mycoides* was sporulated and the solution with spores was heated to 100° C. for ten minutes. The organisms surviving this treatment were thereafter defined as spores. Initially 2.5 g sodium percarbonate was dissolved in 9.8 ml deionized sterilized water at 50° C., whereafter the solution was allowed to cool to room temperature. A series of dilutions was performed from the original solution to the final concentrations of 25%, 12.5%, 6.3%, 3.13% and 0%. 100 microliters of the spore solution (corresponding to about 100 spores) were added to all solutions, whereafter they were incubated for one hour at room temperature. After the incubation the solutions were centrifuged at 12,000×g. Thereafter the pellets were resuspended in water, and the solution was centrifuged again in the same way as previously. This was repeated one more time. After the last centrifugation the pellets were dissolved and distributed in equal quantities on three agar plates for each concentration. Without exception TGEA-plates were used (trypton-glucose-extract-agar, mixed according to the instruction of the producer Unipata Ltd, Basingstoke, Hampshire, England). The plates were incubated during 48 hours at 30° C. Thereafter, the grown colonies were counted by hand.

Results

TABLE 1

Killing of spores by means of a sodium percarbonate solution*

| 25% | 12.5% | 6.25% | 3.13% | 0.0% |
|---|---|---|---|---|
| 0 | 0 | 0 | 11 | 27 |

*Number of colonies per plate

The original concentration of spores added to each concentration of sodium percarbonate was determined by determining the living content (viable count) in separate tests. The mean value demonstrated that the original concentration was 105 spores per 100 microliters. The difference with the zero concentration in the table is due to the losses during the three centrifugations carried out during each test. From this example can be seen that sodium percarbonate with a concentration of 6.25 percent by weight at room temperature is effective in killing spores.

EXAMPLE 2

Growth control and killing of bacteria (performed by FOA)

Test Organisms

Two different product destroying bacteria were isolated from deposits on dairy equipment at Norrmejerier, Umea. One of the isolates was a gram-positive spore-forming bacterium, B.mycoides, see example 1. The other isolate was identified as Pseudomonas spp. Both strains were identified by means of api 20E (Api 20 E bioMeiuex, 69280 Marcy L Etorel, RCS Lyon, France). Moreover, Salmonella typherium LT2A was used as a test organism (Ames B. Zinder N D, Lederberg, J <1952> Genetic exchange in Salmonella J Bacteriol 64:679–669).

a) Minimum inhibiting concentration

Initially a trial test was performed where the concentration range providing inhibition was encircled. As a cultivating medium for both the initial test and the main test were used TGEA-agar plates. During the casting of the plates sodium percarbonate was added in various concentrations. The addition was provided after the autoclaving. As a control TGEA-plates were used without any addition of sodium percarbonate. A constant amount of bacteria were spread onto the cultivating plates containing various concentrations of sodium percarbonate. After the incubation of 24 hours at 30° C., the concentration of bacteria was determined by determining the living content, the bacteria being resuspended in PBS (Phosphate Buffer Saline) to an absorbance corresponding to 1.0 at 650 nm. A serial dilution was thereafter performed from $10^{-1}$ to $10^{-7}$, and 100 µl of the various dilutions were spread onto TGEA-plates without any additions and were incubated at 30° C. during 24 hours. Thereafter the bacteria colonies were counted by hand and the concentration of bacteria was calculated in a way known per se.

Result from an initial test

The result of the initial test shows that no growth could occur for any one of the three tested bacteria from a concentration of 0.10% to 5.0%.

Result of the main test

TABLE 1

Main Test with various Concentrations of Sodium Percarbonate on TGEA-Plates

| Concentration of Sodium Percarbonate per agar Plate[1] | Number of Pseudomonas Colonies in Percent of the original Number[2] | Number of Salmonella Colonies in Percent of the original Number[2] | Number of Bacillus Colonies in Percent of the original Number[2] |
|---|---|---|---|
| 0.00 | 100 | 100 | 100 |
| 0.00 | 100 | 100 | 100 |
| 0.00 | 100 | 100 | 100 |
| 0.005 | 31 | 5 | 9 |
| 0.005 | 35 | 9 | 10 |
| 0.005 | 25 | 5 | 12 |
| 0.010 | 0 | 0 | 0 |
| 0.010 | 0 | 0 | 0 |
| 0.010 | 0 | 0 | 0 |
| 0.025 | 0 | 0 | 0 |
| 0.025 | 0 | 0 | 0 |
| 0.025 | 0 | 0 | 0 |

[1]The concentrations are indicated in percentage by weight
[2]100 percent corresponds for Pseudomonas spp 68 ± 19, for Bacillus 137 ± 16 and for Salmonella 339 ± 127 colonies.

The table shows that a concentration of only 0.01 percent by weight of sodium percarbonate is effective in controlling growth for all tested bacteria.

b) killing of the bacteria

Sodium percarbonate was dissolved in PBS at 50–60° C. and was thereafter allowed to cool to room temperature. A constant amount of the three above mentioned bacteria was mixed in PBC containing various concentrations of sodium percarbonate and was incubated for one hour at room temperature. After the incubation the solutions were centrifuged at 12,000×g. After this, the pellet was resuspended in PBS, and the solution was centrifuged again in the same way as above. This procedure was repeated a further time. After the last centrifugation the pellets were dissolved and distributed in equal amounts on three TGEA-agar-plates for each concentration. The plates were incubated for 24 hours at 30° C. Thereafter grown colonies were counted by hand.

Results

Initially one preliminary test was made to encircle the concentration range where the three different bacteria strains are killed. The results of the main test is shown in table 2.

TABLE 2

Incubation of various Bacteria in various Concentrations of Sodium Percarbonate during one Hour at Room Temperature

| Concentration of Sodium Percarbonate in PBS[1] | Number of Pseudomonas Colonies in Percent of the original Number[2] | Number of Salmonella Colonies in Percent of the original Number[2] | Number of Bacillus Colonies in Percent of the original Number[2] |
|---|---|---|---|
| 0.00 | 100 | 100 | 100 |
| 0.00 | 100 | 100 | 100 |
| 0.00 | 100 | 100 | 100 |
| 0.1 | 100 | 100 | 100 |
| 0.1 | 100 | 100 | 100 |
| 0.1 | 100 | 100 | 100 |
| 0.2 | 100 | 100 | 100 |
| 0.2 | 100 | 100 | 100 |
| 0.2 | 100 | 100 | 100 |
| 0.4 | 0 | 5 | 2 |
| 0.4 | 0 | 5 | 1 |
| 0.4 | 0 | 7 | 1 |
| 0.8 | 0 | 1 | 0 |
| 0.8 | 0 | 1 | 0 |
| 0.8 | 0 | 0.4 | 0 |

[1]The concentrations are indicated in percent by weight
[2]100 percent corresponds for Pseudomonas spp 442 ± 64, for Bacillus 137 ± 16 and for Salmonella 339 ± 127 colonies.

The table shows that a concentration of over 0.8 percent by weight kills bacteria at room temperature.

EXAMPLE 3

Killing of spores on udder fabric cloth

A used udder cloth is placed in a bucket. Thereafter about 5 liters of warm water (<45° C.) and 0.3 kg (about 3.5 dl) of sodium percarbonate powder are added (6 percent by weight).

After at least one hour all spores and bacteria have been killed. The cloths should preferably remain in the solution during 30 minutes before the next milking. The cloths are rinsed in lukewarm water before use.

EXAMPLE 4

Killing of mold spores 0.3 kg (about 3.5 dl) of sodium percarbonate are added to 5 liters of warm water (<45° C.) (6 percent by weight), are stirred and the solution is poured into a low spray gun, and stable boxes, manure groves, walls and if possible roof and the storage spaces for fodder are sprayed. The sprayed solution is left to act for a couple of minutes. No rinsing is required and no dangerous chemical residues are left behind. Even a bad smell from manure disappears effectively by means of the solution.

EXAMPLE 5

Rinsing of a tank

The tank is filled with water and thereafter sodium percarbonate powder is added according to the dosing instructions below. The tank is filled to the brim with water, not necessarily being warm, and is left without any cover for at least 12 hours. Thereafter, the tank is emptied and rinsed with water. Thus, a clean tank is obtained and possibly present algae, yeast fungi and slime bacteria are killed and effectively removed. To remove any slime bacteria which stick to the tank wall a higher concentration between 0.6 and 6 percentage by weight is recommended, depending on the amount of slime bacteria.

The rinsing solution has after 24 hours such a low toxicity that the solution should not create any harmful illness if consumed.

Dosing for various application fields

Fresh water tanks: 250 ml powder per 40 liters of tank volume (about 0.5 percentage by weight)

Sewage tanks: 250 ml powder per 25 liters of tank volume (about 0.8 percentage by weight)

Cesspools: 50 ml of powder should be added

Pump pits: 1 liter to be added to a 100 liters of tank volume.

EXAMPLE 6

Killing of bacteria in drinking-water 0.1 kg of sodium percarbonate are added to 1,000 liters water (<45° C.) (0.01 percent by weight). Leave to act for one hour. After one hour, the bacteria have been killed and after 24 hours the water is drinkable (see example 7a).

The sodium percarbonate might e.g. be added to the water in form of an effervescent tablet, the tablet being e.g. so adapted that one tablet is giving the desired concentration in 5 liters of water.

EXAMPLE 7

Degradation of sodium percarbonate in a water solution (performed by FOA)

a) Stability is set at about 50° C. The content of active oxygen in the sodium percarbonate solution is determined by means of iodometric titration (A I Vogel, *Quantative inorganic analysis*, page 363). 20.0 mg sodium percarbonate were dissolved in 200 ml water (100 mg/l, 0.001 percentage by weight) at 50° C. while being slowly stirred. When all had been dissolved, the measuring was started. A 10 ml sample was taken each time and the concentration of active oxygen and hydrogenperoxide was determined.

| Time in Minutes | H$_2$O$_2$ ppm | Percentage of active Oxygen |
| --- | --- | --- |
| 2 | 11.2 | 73 |
| 10 | 7.6 | 50 |
| 20 | 3.7 | 24 |
| 30 | 1.1 | 7 |
| 40 | 12 | 8 |
| 60 | 0.5 | 3 | b) Stability at 30° C. after dissolving at 60° C.

50 mg sodium percarbonate were dissolved in 500 ml water (100 mg/l, 0.01 percent by weight) at 60° C. The solution was allowed to cool down to 30° C. and was kept at this temperature. The concentration of active oxygen and hydrogen peroxide was determined after 30 and after 60 minutes. The test volume was 5 ml.

| Time in Minutes | H$_2$O$_2$ ppm | Percentage of active Oxygen |
| --- | --- | --- |
| 0 | 11.0 | 72 |
| 30 | 10.4 | 68 |
| 60 | 8.6 | 56 |

The results show that hydrogen peroxide is degraded down to harmless levels within one hour at 50° C. At lower temperatures the degradation is slower.

To sum up, the present description shows that spores and other difficult to control microorganisms are effectively killed with sodium percarbonate at 6.25 percent by weight. Furthermore it is shown that algae, yeast fungi and slime bacteria can be effectively killed and removed with sodium percarbonate at a concentration of 0.5 percent by weight. Moreover it is shown that a drinking-water free of bacteria can be obtained by means of adding sodium percarbonate at 0.01 percent by weight at an elevated temperature. In all cases no toxic residues are formed.

The sodium percarbonate thus provides an efficient agent adapted to the environment for killing both spores, algae, and bacteria and fungi.

I claim:

1. A method for the control of spores, yeast fungi and bacteria in drinking water, said method comprising the step of bringing an active amount of a sodium peroxy compound consisting essentially of sodium percarbonate and sodium peroxide into contact with said spores, yeast fungi and bacteria, and killing said spores, yeast fungi and bacteria in drinking water.

2. The method of claim 1, wherein the active amount of the sodium peroxy compound is about 5 to 10 percent by weight.

3. The method of claim 2, wherein the active amount of the sodium peroxy compound is about 6 to 7 percent by weight.

4. The use of a sodium peroxy compound consisting essentially of sodium percarbonate and sodium peroxide for controlling spores, yeast fungi and bacteria, comprising the step of bringing the spores, yeast fungi and bacteria into contact with an active amount of the sodium peroxy compound and killing said spores, yeast fungi and bacteria in drinking water.

5. The use according to claim 4, wherein said active amount of the sodium peroxy compound is between 5 and 10 percent by weight.

6. The use according to claim 5, wherein said active amount of the sodium peroxy compound is 6 to 7 percent by weight.

7. The use of a sodium peroxy compound consisting of at least one of sodium percarbonate and sodium peroxide for controlling yeast fungi and slime bacteria in drinking water, comprising the step of bringing the yeast fungi and bacteria into contact with an active amount of the sodium peroxy compound and killing said yeast fungi and bacteria.

8. The use according to claim 7, wherein said active amount of the sodium peroxy compound is 0.3 to 1.0 percent by weight.

9. The use according to claim 8, wherein the active amount of sodium peroxy compound is 0.4 to 0.6 percent by weight.

10. The use according to claim 7, wherein said step of bringing the yeast fungi and bacteria into contact with the sodium peroxy compound further brings spores into contact with the sodium peroxide compound and kills the spores.

11. The use according to claim 10, wherein said active amount of the sodium peroxide compound is from 5 to 10 percent by weight.

12. The use according to claim 11, wherein said active amount of the sodium peroxide compound is from 6 to 7 percent by weight.

13. The use of a sodium peroxy compound consisting of at least one of sodium percarbonate and sodium peroxide for controlling yeast fungi and slime bacteria, comprising the step of bringing the yeast fungi and bacteria into contact with an active amount of the sodium peroxy compound and killing said yeast fungi and bacteria.

14. The use according to claim 13, wherein said active amount of the sodium peroxy compound is 0.3 to 1.0 percent by weight.

15. The use according to claim 14, wherein the active amount of sodium peroxy compound is 0.4 to 0.6 percent by weight.

16. The use according to claim 13, wherein said step of bringing the yeast fungi and bacteria into contact with the sodium peroxy compound further brings spores into contact with the sodium peroxide compound and kills the spores.

17. The use according to claim 16, wherein said active amount of the sodium peroxide compound is from 5 to 10 percent by weight.

18. The use according to claim 17, wherein said active amount of the sodium peroxide compound is from 6 to 7 percent by weight.

* * * * *